(12) United States Patent
Papp

(10) Patent No.: US 8,313,791 B2
(45) Date of Patent: Nov. 20, 2012

(54) MANDRELS SUPPORTING MEDICAL DEVICES DURING PROCESSING OF THE MEDICAL DEVICES

(75) Inventor: John E. Papp, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 421 days.

(21) Appl. No.: 12/752,983

(22) Filed: Apr. 1, 2010

(65) Prior Publication Data

US 2011/0245908 A1    Oct. 6, 2011

(51) Int. Cl.
- *A61F 2/06* (2006.01)
- *A61F 2/82* (2006.01)
- *A61L 33/00* (2006.01)
- *B05D 7/00* (2006.01)
- *B23Q 1/25* (2006.01)

(52) U.S. Cl. ............... 427/2.25; 623/1.15; 623/1.16; 269/47

(58) Field of Classification Search ............ 427/2.25; 623/1.15, 1.16; 269/47
See application file for complete search history.

(56) References Cited

U.S. PATENT DOCUMENTS

| | | |
|---|---|---|
| 4,733,665 A | 3/1988 | Palmaz |
| 4,800,882 A | 1/1989 | Gianturco |
| 4,886,062 A | 12/1989 | Wiktor |
| 5,507,768 A | 4/1996 | Lau et al. |
| 5,514,154 A | 5/1996 | Lau et al. |
| 5,569,295 A | 10/1996 | Lam |
| 7,572,336 B2 | 8/2009 | Van Sciver et al. |
| 2006/0035012 A1 | 2/2006 | Pacetti et al. |
| 2008/0311280 A1 | 12/2008 | Chen et al. |
| 2009/0035449 A1 | 2/2009 | Chen et al. |
| 2011/0245908 A1* | 10/2011 | Papp .................. 623/1.16 |

OTHER PUBLICATIONS

U.S. Appl. No. 12/497,133, filed Jul. 2, 2009, Bobson et al.
U.S. Appl. No. 15/554,671, filed Sep. 4, 2009, Pacetti et al.
U.S. Appl. No. 12/554,820, filed Sep. 4, 2009, Gillick et al.

* cited by examiner

*Primary Examiner* — Timothy Vanoy
(74) *Attorney, Agent, or Firm* — Squire Sanders (US) LLP

(57) ABSTRACT

An apparatus and method for applying a coating composition to a stent. A mandrel for supporting the stent has one or more drive pins and other supporting structure that loosely supports the stent, in an unstable position. The support permits freedom of movement of the stent relative to the mandrel to cause the stent to frequently re-position itself over the mandrel during a spraying process. When a coating composition is applied, the stent randomly or periodically moves about relative to the mandrel due to intermittent contact between the stent and the rotating mandrel and fluidic forces applied through the sprayed coating composition.

22 Claims, 3 Drawing Sheets

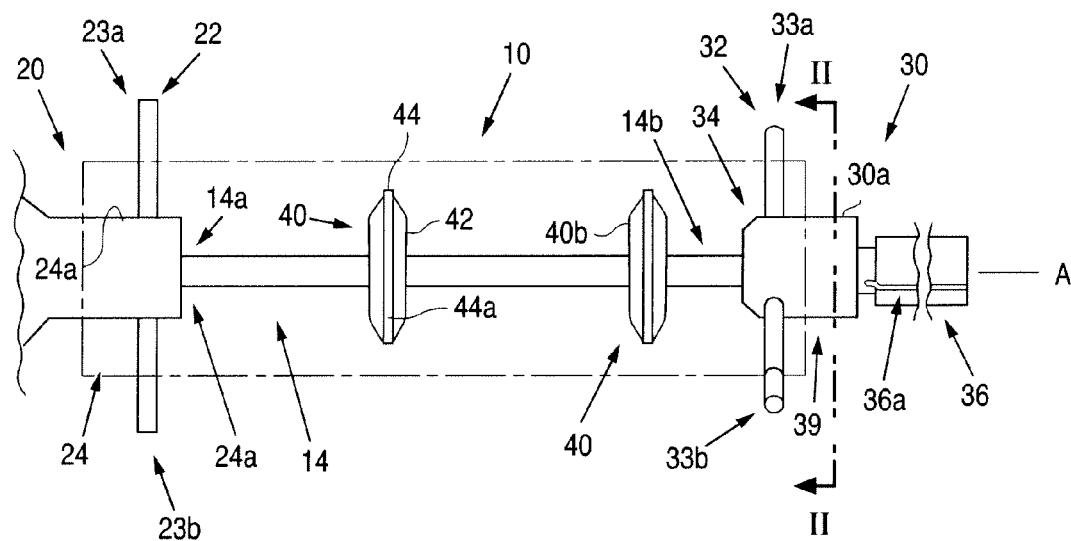
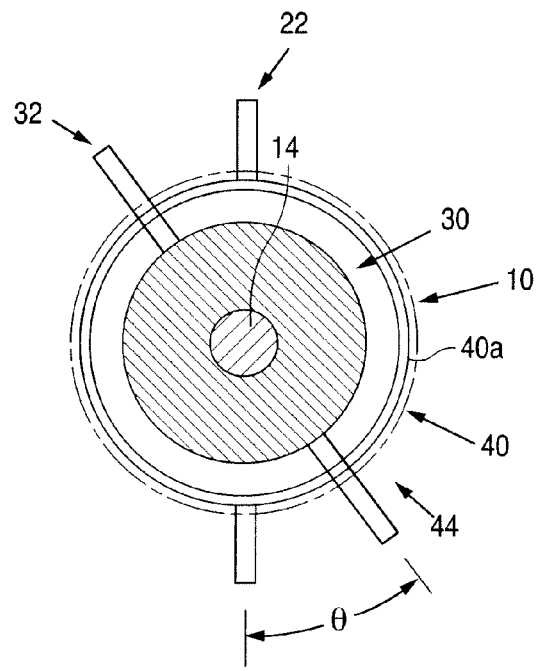

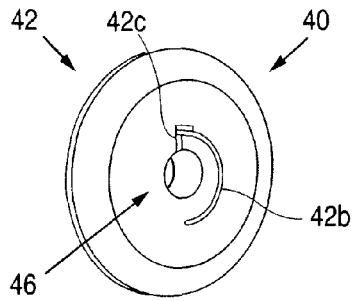 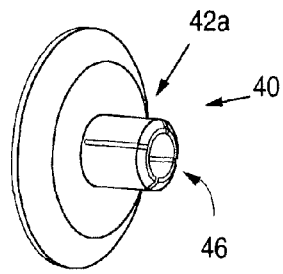
FIG. 5   FIG. 6
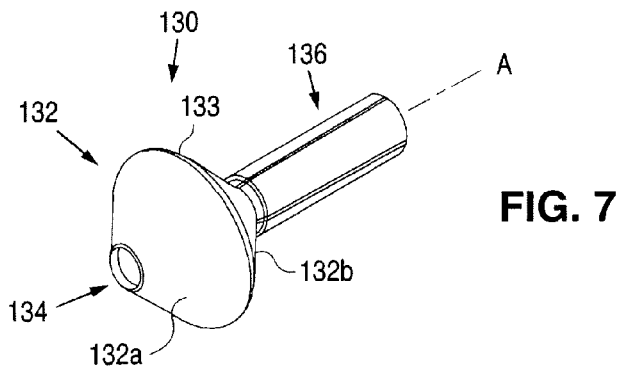
FIG. 7
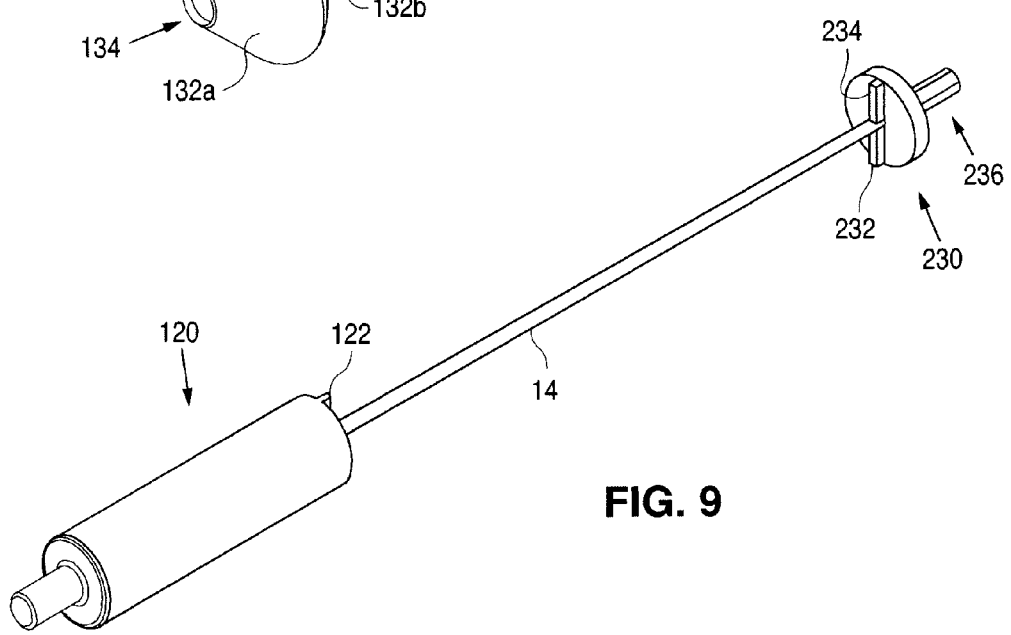
FIG. 9

MANDRELS SUPPORTING MEDICAL DEVICES DURING PROCESSING OF THE MEDICAL DEVICES

BACKGROUND OF THE INVENTION

1. Field of the Invention

The present invention relates to drug-eluting medical devices; more particularly, this invention relates to support structure for medical devices. The support structure is used to support the medical device during processing of the medical device, in particular, when a coating is applied to the medical device.

2. Background of the Invention

Balloon expandable, or self-expanding stents are used to treat a variety of conditions, or prevent conditions from re-occurring within the body. For example, in percutaneous transluminal coronary angioplasty (PTCA), a balloon catheter is inserted through a brachial or femoral artery, positioned across a coronary artery occlusion, and inflated to compress the atherosclerotic plaque to open, by remodeling, the lumen of the coronary artery. The balloon is then deflated and withdrawn. Stents are used to prevent re-occurrence of conditions such as thrombosis and restenosis, which may occur several months after an angioplasty procedure is performed.

The treatment of a diseased site or lesion with a stent involves both delivery and deployment of the stent. Stent delivery refers to introducing and transporting the stent through an anatomical lumen to a desired treatment site, such as a lesion in a vessel. An anatomical lumen can be any cavity, duct, of a tubular organ such as a blood vessel, urinary tract, and bile duct. Stent deployment corresponds to expansion of the stent within the anatomical lumen at the region requiring treatment. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen with the stent remaining at the treatment location.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend and applied to the stent by immersing the stent in the composition or by spraying the composition onto the stent. The solvent is allowed to evaporate, leaving on the stent strut surfaces a coating of the polymer and the therapeutic substance impregnated in the polymer. Depending on the application and volatility of the solvent, forced air drying may also be used to remove the solvent from the coating and arrive at a desired release rate for the impregnated therapeutic agent into the body.

It is known that some methods for coating stents do not produce an ideal, or defect-free coating over a surface of the stent where the therapeutic agent is intended to take effect. Coating defects may include non-uniform surface characteristics, such as bare spots and flaking. Coating defects can also serve as an initiation site for later-developed peeling or flaking that produces embolic debris. Rough surfaces generated by, and stagnant regions of blood flow produced nearby flaps or packets formed by coating defects can serve as a nidus for thrombus formation. Furthermore, coating defects produce variations in the intended amount, concentration, and release rate of the drug from the stent coating, further complicating or minimizing the effectiveness of therapeutic agents.

Methods for spray coating a stent with polymer-drug dissolved in a solvent include mounting the stent on a mandrel to support and rotate the stent while it is being sprayed with the drug-polymer composition. Examples of prior mandrel designs constructed for this purpose are disclosed in U.S. patent application Ser. Nos. 12/497,133; 12/027,947; 12/554,671 and 11/764,006 (U.S. Pat. No. 7,897,195); U.S. Pat. No. 7,572,336; and U.S. Pub. No. 2006/0035012.

In view of the foregoing, there is a continuing need for coating methods and systems that further minimize stent coating defects.

SUMMARY OF THE INVENTION

The invention improves on the art by providing an apparatus and method for applying a coating composition to a surface of a stent in which there is a surprisingly reduced number of instances in which coating defects appear over the surface of the stent. The art has previously sought ways to minimize instances of coating defects, primarily in areas where the stent fixture, e.g., a mandrel support, contacts surfaces of the stent where a uniform and consistent coating composition is desired.

As discussed earlier, coating defects include flaking or buildup of a coating composition near support areas where the stent was supported during a coating process. Coating defects also refers to those areas of the stent is untouched, but where sprayed composition does not adequately form over surfaces due to some obstruction or "shadowing" of a stent surface while the coating composition is being applied. For example, when a supporting structure for the stent is disposed between a surface of the stent and the spray nozzle while the stent is being coated, this obstruction or shadowing of the stent surface from the spray nozzle will limit the degree to which the stent surface may receive the same coating as other surfaces of the stent. Thus, the continued need for minimizing coating defects refers to, not only those areas where the stent is placed in direct contact with the supporting structure, but also those areas that are not exposed to, or have unequal exposure to the spray nozzle as compared to nearby surfaces of the stent.

According to the invention, a mandrel supports a stent intermittently, making brief contact with different surfaces of the stent as the stent is being rotated beneath a spray nozzle producing, over the course of a spraying period, a more uniformly applied coat over the surface that is directly exposed to the spray from the spray nozzle and also the stent surfaces that will make contact with the support, as well as surfaces that do not make contact but will occasionally become shadowed or blocked from the spray nozzle due to the presence of a support structure. As the stent is rotates, the stent is constantly re-positioned on the mandrel so that all stent surfaces are more fully exposed to the spray nozzle to achieve a uniform coating. The motion of the stent relative to the mandrel is described as one where contact surfaces between stent and mandrel are never the same. They are constantly changing. Moreover, obstructing surfaces of the mandrel between the stent and spray nozzle are never constant either. The result is that the applied coating at the occasional contact areas is allowed to dry under the drying nozzle and build up in thickness as multiple coats are applied. Also the constant jostling of the stent on the mandrel prevents the stent coating from adhering the stent and mandrel together. Whenever a stent and mandrel are adhered together, separation of the two causes coating defects that include, cracks and tears.

The loose, or unstable nature of the stent when supported on a rotating mandrel facilitates the desired relative motion between stent and mandrel. Indeed, the changing position of the stent relative to the mandrel occurs in six degrees of freedom, meaning that the stent will experience rotation about three axes and translation in three dimensions relative to the mandrel as the mandrel rotates and the stent abuts surfaces of the mandrel restraining its movement. The movement about axes other than the mandrel rotation axis is limited, naturally, to keep the stent on the mandrel. Nevertheless, the movement is present and serves to expose surfaces of the stent, by constantly repositioning the stent on the mandrel, so that surfaces that would otherwise develop coating defects because the stent is fixed in one or degrees of freedom relative to the mandrel are not present in the stent support of the invention. The result is that over the period when the coating composition is applied there is a net uniform coat everywhere, thereby improving the coating quality both in areas where the stent has touched the mandrel and where the mandrel tends to obstruct or shadow stent surfaces.

In accordance with the foregoing, there is an apparatus and method of the invention that substantially improves upon the art.

In one aspect, a method for spraying a coating composition on a stent, the stent having a first end and opposing second end and respective first and second ring structures disposed at each end, a bore, a bore diameter and a bore axis. The method includes mounting the stent on a mandrel support having a rotation axis including disposing a collar of the mandrel within the stent bore, the collar having a diameter that is less than the bore diameter so that the stent is free to move laterally relative to the collar, the stent resting on a surface of the collar, and the mandrel including a drive pin; rotating the mandrel; spraying the coating composition on the stent; and applying a force to the stent by the drive pin of the rotating mandrel striking the first end of the stent to thereby impart rotating motion to the stent about the rotation axis, whereupon after the stent has rotated through an angle the stent separates from the collar and the drive pin.

In another aspect a method for spraying a coating composition includes the steps of positioning a drive pin of the mandrel between struts forming one of the valleys of the first ring structure; positioning an abutting end of the mandrel near the second ring structure, wherein a gap is formed between the abutment and the second ring structure or the drive pin and the struts forming the valley of the first ring structure; coupling the stent and mandrel to a rotary drive, the rotary drive adapted for rotating the mandrel about a rotational axis; rotating the mandrel about the rotational axis; applying the coating composition to the stent; wherein the stent is displaced along the rotational axis and lateral to the rotational axis relative to the mandrel as the stent rotates.

In another aspect a stent is supported on a mandrel, the stent having a ring structure at a first and second end of the stent, each ring structure having a repeating pattern of peaks and valleys. The apparatus includes a first mandrel portion adapted for being coupled to a rotary drive; a second mandrel portion; a rod extending parallel to a longitudinal axis, between and connecting the first and second mandrel portions; a collar supported by the rod and disposed between the first and second mandrel portions for supporting the stent; a first drive pin extending from the first mandrel portion and in a direction approximately perpendicular to the longitudinal axis; and an abutment of the second mandrel portion for making abutting contact with the stent; wherein the drive pin and/or abutment are spaced a distance from surfaces of the stent to enable the stent to freely displace relative to the drive pin and abutment both along, and laterally of the longitudinal axis direction.

In another aspect a method for forming a coating over a surface of a stent includes the steps of providing a first and second mandrel portion, the first mandrel portion including a base adapted for being coupled to a rotary drive and a rod that extends along a longitudinal axis from the base to a rod end, and a drive pin that extends from the base along a direction approximately perpendicular to the longitudinal axis, and the second mandrel portion adapted for being positioned on the rod and including an abutment, and mounting the stent on the first mandrel portion including placing the stent over the rod and positioning the drive pin within a valley of the stent's ring structure at the stent's first end; positioning the second mandrel portion on the rod including placing the second mandrel portion abutment relative to the stent second end such that a gap exists between the abutment and the second end of the stent, thereby permitting the stent to freely displace along the longitudinal axis between the drive pin and abutment; coupling the first mandrel portion to the rotary drive and rotating the stent; and applying a coating substance to the rotating stent.

In another aspect there is a support including a mandrel. The mandrel is intended to support a stent during a coating operation. The support includes a first mandrel portion adapted for being coupled to a rotary drive; a second mandrel portion; a rod extending parallel to a longitudinal axis, between and connecting the first and second mandrel portions; a collar supported by the rod and disposed between the first and second mandrel portions; a first drive pin extending from the first mandrel portion and in a direction approximately perpendicular to the longitudinal axis; and optionally an abutment of the second mandrel portion for making abutting contact with the stent. The pin and abutment are capable of being spaced a distance from surfaces of the stent to enable the stent to freely displace relative to the drive pin and abutment both along, and laterally of the longitudinal axis direction. Optionally, the mandrel can be devoid of a second mandrel portion, in which case the mandrel may be coupled to a rotary drive orienting the mandrel at least partially along a direction that gravity acts.

In accordance with another aspect of the invention, a stent mandrel support consists of one or more drive pins, a rod, one or more collars, a base member and optionally an endcap. According to this embodiment only one or more collars, drive pins, a base, a rod and, optionally an endcap support the stent. There is no cage used to retain the stent on the mandrel. Nor is there other structure, other than one or more pins and collars that prevent the stent from being completely and permanently removed from the support during a drying process. During a coating process, the stent makes contact with only one or more collars and only one or more pins. Optionally, the stent may also make contact with an endcap.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

BRIEF DESCRIPTION OF THE DRAWINGS

FIG. 1 is a partial side view of a mandrel and stent supported by the mandrel. The mandrel illustrated shows a base, endcap, rod and collar assembly. The stent is depicted here as a cylindrical body in phantom.

FIG. 2 is a view of the mandrel and stent of FIG. 1 when viewed in the direction indicated as II-II in FIG. 1. This view is taken in a direction perpendicular to a longitudinal or rotation axis of a rod of the mandrel.

FIG. 5 is a perspective view of a preferred embodiment of the collar of the mandrel of FIG. 1.

FIG. 6 is an alternative embodiments of the collar of the mandrel of FIG. 1.

FIG. 7 is an alternative embodiment for the endcap of the mandrel of FIG. 1.

FIG. 9 is an alternative embodiment of a mandrel assembly. This embodiment shows an alternative embodiment for a base and endcap of the mandrel of FIG. 1.

DETAILED DESCRIPTION OF EMBODIMENTS

When spraying stents with a drug/polymer mixture it is critical to minimize the defects in the coating caused by the contact of the stent to the spraying mandrel on which it sits while being sprayed. When a drug eluting stent (DES) is implanted, coating defects can cause adverse reactions in the body. In addition, defective coatings can break off and form emboli, or protruding coating can be an initiation point for thrombus formation. Uncoated areas will not contain the intended drug, which can lead to restenosis.

According to the disclosure various embodiments of a mandrel for loosely holding a stent during a coating process are provided. The support imparts an almost one-to-one rotation between the supported stent and a rotary drive, which rotates the stent during a spraying or drying application. An "almost" on to one rotation means that there is slight difference in the rotation displacement and/or rate, relative to the mandrel. This motion may also be understood as a rotational slip between the stent in mandrel, which occurs as a result of a gap or space intentional left between the stent and one or more drive pins that impart rotation to the stent. There is also a loose fit in translational directions that further promotes a stent support structure where the contact points are constantly changing as the stent rotates. According to the embodiments the coupling between stent and mandrel may be described as a limited motion restraint permitting limited, six degrees of freedom movement of the stent relative to the mandrel.

A stent typically has a plurality of undulating, e.g., sinusoidal, ring structures that collectively provide a radial stiffness for the stent, and struts connecting the cylindrical elements. Lengthwise the stent is supported typically by only the flexural rigidity of slender-beam-like linking or connecting elements, which structure may give the stent a desired longitudinal flexibility. Examples of structure and surface topology of a stent are disclosed by U.S. Pat. Nos. 4,733,665, 4,800,882, 4,886,062, 5,514,154, 5,569,295, and 5,507,768. Additionally, this disclosure adopts the stent structure terminology of FIGS. 1-3, paragraphs [026] through [035], et seq. of U.S. application Ser. No. 12/554,671.

Figure 3:
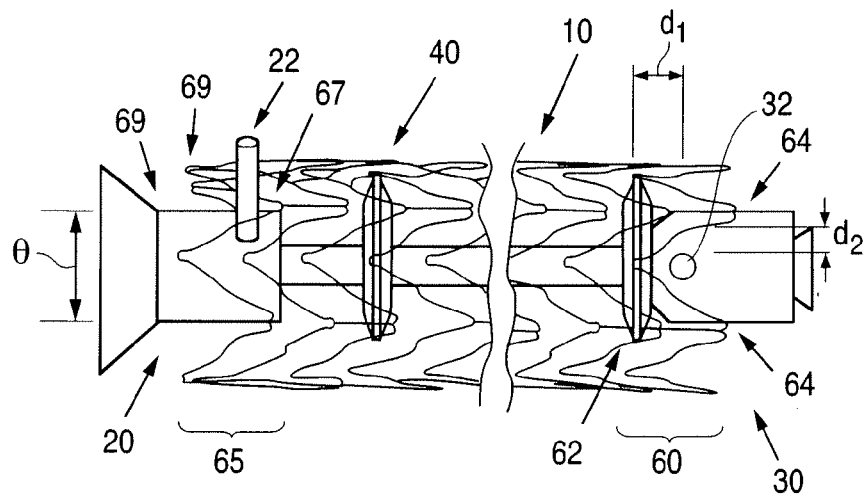
FIG. 3 is a partial side view of the mandrel with a stent supported thereon. In this drawing a stent pattern is illustrated and describes one preferred arrangement between the outer ring structures of the stent and pins, which are used to restrain the stent and impart forces by striking the stent to cause it to rotate with the mandrel during a coating or drying process for the stent.

Referring to FIGS. 1-4 there is a first disclosure of a mandrel support for a medical device, in this example a stent 10, which is shown in phantom in FIGS. 1 and 2. FIG. 3 shows a partial view of the stent 10 structure supported by the mandrel with the stent's structural elements illustrated for purposes of discussing the support of the stent by the mandrel, as described in greater detail below.

A base 20 of the mandrel has a unitary body forming a generally cylindrical-shaped end 24, handle 26, tapered section extending between the end 24 and handle 26, and a connecting end 28. The connecting end 28 forms a fitting for connecting the base 20 to a rotary drive of an electric motor. When coupled to the rotary drive (not shown), the drive rotates the mandrel about the longitudinal axis during a stent coating or drying process. An example of a stent coating and drying apparatus suitable for use with the mandrel and supported stent 10 illustrated in FIGS. 1-4 is described in my U.S. application Ser. No. 12/554,820.

A rod 14 of the mandrel is received within an opening of a channel formed in the base 20 (not shown) so that the rod 14 extends left to right in FIG. 1 in a longitudinal direction (as illustrated by longitudinal axis A in FIG. 1). A first end 14a of the rod 14 is securely fixed within this channel so that the rod 14 may be supported from the base 20 as a cantilever.

An endcap 30 of the mandrel is a unitary piece having a generally cylindrical-shaped end 34, slotted end 36 and channels extending through ends 34 and 36. A channel of end 34 is slightly larger than the outer diameter of the rod 14 so that end 34 may easily slide over rod 14. Endcap 30 may be slide over end 14b of rod 14 and located a desired distance from end 24, which distance is determined from the length of the stent 10, as described in greater detail below. The slotted end 36 has a channel diameter smaller than the rod 14 outer diameter. Longitudinal slots 36A formed in the slotted end 36 allow deflectable walls (the walls become deflectable by the presence of the longitudinal slots) of the slotted end 36 to deflect outwardly as the rod 14 is forcibly inserted into the channel of the slotted end 36. As such, the biasing forces of the slotted end 36 walls against the rod 14 surface permits the endcap 30 to sufficiently resist movement along the rod 14 by friction between the rod 14 and deflectable walls of the slotted end 36.

One or more collars 40 of the mandrel are received on the rod 14 and disposed between the ends 24 and 34. A collar 40 includes a body having a resilient portion 42 and a ring 44 defining an outer diameter of the collar that makes contact with the stent 10 bore on surface 44a. Ring 44 may be formed by a metallic material to facilitate cleaning of surface 44a as coating material may tend to build up on this surface. An aperture formed in the resilient portion 42 receives the rod 14. The aperture has a diameter smaller than the outer diameter of the rod 14 so that the collar may be snugly retained at a position along the rod 14, the fit being sufficient to resist motion along the rod 14. The collar 40 resilient portion 42 may be formed by an elastic material so that the rod 14 may be forcible pressed through the aperture. In other embodiments the resilient portion may have a slotted tubular end 42a (FIG. 6), which functions in a similar manner as slotted end 34 described above, or a combination half-circle cut 42b and secondary cut 42c to the opening 46 of the resilient portion 42 (FIG. 5) to provide a desired retaining force resisting movement of the collar 40 along the rod 14. In either of these embodiments, a resilient structure, i.e., a slotted tube or deflectable semi-circle, may function in a manner similar to a resilient portion 42 formed of an elastic material.

Pins 22 and 32 are received in openings formed in the ends 24 and 34, respectively. As depicted in FIGS. 1A and 1B, pins 22 and 32 extend approximately perpendicular to the axis A and have respective ends 23a, 23b and 33a, 33b. In this embodiment pins 22 and 32 extend through the respective ends 24 and 34, although they may alternatively extend from only one side of the ends 24, 34, e.g., pin 22 may have only end 23a or 23b extending from the end 24 and pin 32 may have only end 33a or 33b extending from the end 32.

The collars 40 are preferably removable from the rod 14 to assist with cleaning during stent coatings. The collars 40 may be removed from, then placed back on the rod 14 numerous times, or they may be treated as disposable items. The number of collars 40 to be used can be a function of the stent length. As the ratio of a stent's length to its diameter increases (assuming the same wall thickness and material properties), there is an increased tendency for the stent to sag or bow near its midsection unless the stent body is adequately supported near its mid-span by additional collars. Avoidance of these conditions is desirable to prevent the stent bore from contacting the rod 14 (or ends 24, 34) as it rotates and displaces due to its loose fit on the mandrel. Moreover, when the stent is moved from the sprayer to the dryer application, the transient fluid forces associated with a forced air dryer can cause the stent to bounce about uncontrollably unless it is adequately supported. This condition is described in more detail in my U.S. application Ser. No. 12/554,820.

Preferably, endcap 30 may be rotationally positioned relative to end 24 to accommodate a particular stent design or form a preferred supporting structure for the stent 10. Referring to FIGS. 2 and 3, pin 32 is oriented about 30 degrees (angle theta is about 30 degrees) from pin 22, which corresponds approximately to the angular spacing between valleys 67 and 62 of ring structures 65 and 60, respectively, of the stent 10.

Figure 4:
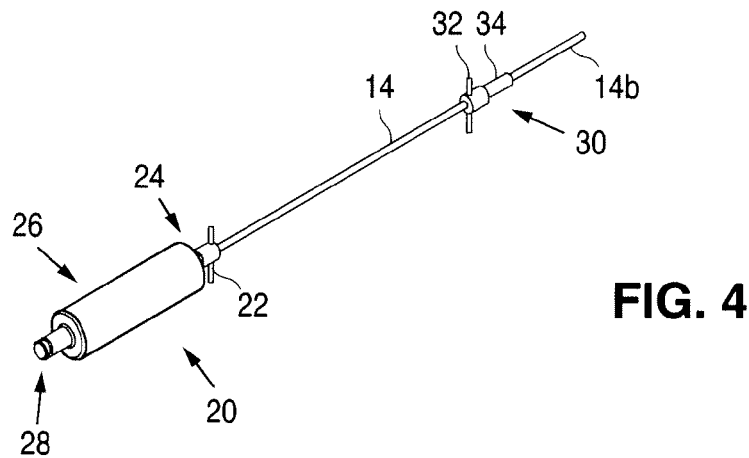
FIG. 4 is a perspective view of the mandrel of FIG. 1 without the supporting collars or the stent shown.

Pins 22 and 32 may be angularly spaced at angles greater than 30 degrees, or they may not have any angular spacing between each other, as depicted in FIG. 3. The angle selected may be based on the angular spacing between a valley on a near or first end of the stent and the nearest valley on the far or second end of the stent. Thus, in the case of FIG. 2, for the adjacent valleys between first and second ends being chosen for drive pin placement, the angle theta illustrated would correspond to the distance between the adjacent valleys and distance between the drive pins. The angle theta may be 30, 60 or 90 degrees. FIG. 4 is a perspective view of the rod 14, base 20 (with handle 26 and connector 28 shown), endcap 30 and pins 22 and 23. In this arrangement, pins 22 and 32 aligned with each other.

The stent 10 may be mounted to the mandrel in the following manner. The mandrel is first orientated in a position so that rod 14 is mostly extending vertical, or at least partially along the direction of action for gravity. The collars 40 are placed on the rod 14. Then the stent 10 is slipped over the rod and allowed to come to rest by abutment with the pin 22. Then the second end 30 is slipped over the rod and positioned so that the pin 32 (or endcap surface 132a, in the case of endcap 130 being used in place of endcap 30) is located a slight distance from the adjacent end of the stent 10 to provide the gaps d1 and d2. Now the stent is mounted to the mandrel. The connector 28 of the base 20 is then coupled to the rotary drive.

As alluded to above, the stent 10 is supported on the mandrel by a loose fit. According to one aspect of the invention, a mandrel support is configured for intentionally providing an unstable support for the stent, meaning that the stent is supported in such a manner as to encourage uncontrolled or frequent movement of the stent linearly, i.e., along the axis A or perpendicular to this axis, as well as rotationally. Freedom of movement along, or perpendicular to the axis A may be understood by noting that the pins 22 and 32 are spaced from each other in such a manner that a gap d1 (FIG. 3) exists between pin 32 and abutting surfaces of struts of the ring structure 60, that are connected by bending elements (i.e., the apex of the valley 62 of FIG. 3). Since this gap exists, the stent 10 may freely translate over the distance d1, along the direction of the axis A and perpendicular to it, due to the presence of a second gap d2 as well. The gaps d1 and d2 may be about ½ way or midway between struts forming the valley, and midway between the lowest point in the valley and adjacent peaks, respectively. The motion of the stent relative to the pins 22, 32 is allowed because the collars 40 have a perimeter or diameter that is less than the stent 10 bore diameter. The collars 40 prevent the stent from striking the ends 24, 34 in FIG. 1, the collar 40 diameter is greater than that of the ends 24, 43). But the collars 40 allow the stent to freely move relative to pins 22, 23 because the bore size is greater than the collar 40 size as shown in FIGS. 1-3.

A loose coupling in rotation between stent and mandrel exists, to facilitate a slight rotational slip and translation along the mandrel axis. The pins 32, 22 may be thought of as drive pins, which drive the stent in rotation as the pins rotate about the axis A and then strike surfaces of the stent to carry it through a limited rotational range. The gaps d1, d2 allows the contact point between the pin 22, 32 and stent to change as the mandrel and stent rotate and the stent repositions itself on the collars 40. When the stent rotates through an angle by the force applied to it by the drive pin, the stent will eventually separate from the drive pin and reposition itself on the collar. As will be appreciated, this movement of the stent can cause the stent to move through an angle relative to the mandrel about the rotational axis. For example, for the stent pattern shown in FIG. 3, the angle of relative movement, or slip, may be up to about 10 degrees after the stent has been repositioned and separates from the drive pin and collar.

As can be appreciated from FIG. 3, the gap d2 between the pin 32 and struts forming the valley 62 allows variable positioning between surfaces of the pin 32 and surfaces of the stent struts on either side of the pin 32. As the mandrel rotates via its coupling to the rotary drive, the stent will maintain its position until the pin comes into contact with the strut, at which point the stent begins to rotate with the strut. This direct, surface to surface contact between the stent and the pin is maintained until the stent changes position due to the repositioning of the stent bore surface on the collar 40 (as described above) and/or the fluidic forces of the composition striking the stent surfaces jostle the stent. When this happens, the pin can separate from the stent strut to produce intermittent changes in the contact points between the pin 32, 22 and the stent. Changes in stent-mandrel contact may occur simply as a result of fluidic forces acting on the stent as the coating is applied. Since resistance to changes in position of the stent relative to the mandrel is very minimal, the direction of the spray may alone be sufficient to cause the stent to frequently move about on the mandrel.

As can be further appreciated from the embodiments, the mandrel according to the embodiments may permit the stent 10 to translate in each of three orthogonal translational directions, in addition to three directions of rotation. The fit, as mentioned earlier, is like a limited motion restraint, or fit for each of six degrees of freedom for the stent body. The gaps or separation between the stent 10 and mandrel support surfaces (gaps d1, d2 and spacing between collars 40 and the bore surfaces), permit limited, or restricted movement of the stent relative to the mandrel as the stent is rotated by the mandrel. Although the motion may appear slight in some directions, it is known that the effect on the coating quality over the course of a spraying period is significant, and better than if the freedom of movement as described above were not allowed to happen.

Describing the movement somewhat differently, as the stent rotates with the mandrel (through abutment with the pin 22 and 32) the stent 10 longitudinal axis oscillates, or moves randomly about the rotation axis A as surfaces of the stent bore impact different surfaces of the collar 40 while the stent is sprayed. For example, for the mandrel and stent 10 orientated so that gravity acts perpendicular to the axis A, the stent will change its contact points with the collars 40 as the stent rotates through angles less than 180 degrees, as a result of gravity causing the rotating stent to fall down on different contact points 44a of the collars 40. Over the course of the spraying period, the stent and mandrel axes thus move relative to each other, in an oscillatory or random way. The stent 10 is also seen to change position, not insignificantly, on the collars 40 as a result of the coating material being sprayed onto the stent and loose fit. The stent is seen to rotate slightly differently from the mandrel, about three axes (predominantly about the rotation axis, naturally) and translate along and perpendicular to the rotation axis in a somewhat random motion due to the transient nature of the fluidic forces acting on the stent as the coating composition is sprayed. Again, the forces of the fluid contacting the stent can move the stent because the stent is loosely held in six degrees of freedom on the mandrel.

For example, in the case of a 90 degrees separation between drive pins located near each end of the stent, the stent would rotate through the force applied by one drive pin that has struck the stent, then after the stent rotates about 90 degrees the stent drops to a new position on the collar 40 (through gravity) then the other drive pin strikes the stent to cause it to rotate further. As this motion is imparted to the stent, the spray imparts fluidic forces on the stent that produce net forces on the stent in directions lateral of the rotation axis, which cause rotational motion of the stent about lateral axes, and translational motion in three directions.

In an alternative embodiment of the mandrel the assembly is substantially the same as shown and described in connection with FIGS. 1-3, except that the endcap 30 does not include the pin 32. Instead, endcap 30 may take the form of endcap 130 depicted in FIG. 7. Endcap 130 includes opposed bulbous, or conical shapes 132a, 132b having a circular perimeter 133 dividing the two shapes. The endcap 130 is received on the rod 14 by inserting the rod through a channel that extends through the endcap 130. A slotted end 136 is provided to serve the same function as in the case of the slotted end 36 of the prior embodiments.

In one embodiment the endcap 130 replaces the endcap 30 illustrated in FIG. 1. Thus, for this embodiment there is only the pin 22 of the base 20, which may be received within the valley 67 of the stent ring structure 65 at this stent end, as described earlier. The second ring structure 60 is supported on the bulbous or conical surface 132a of the endcap 130. In this embodiment, the stent is not forced to rotate with the mandrel (or restrained in rotation relative to the mandrel) by engagement with an butting surface, e.g., a pin, present at the endcap 130. Rather, the end of the stent 10 having ring structure 60 may freely rotate relative to the endcap 130.

Figure 8:
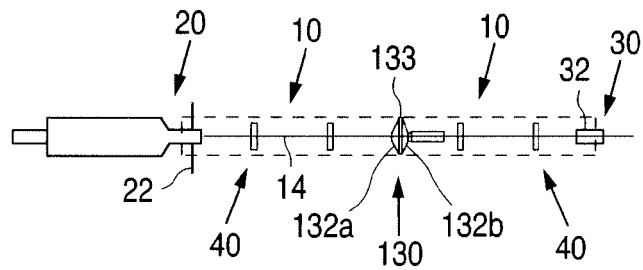
FIG. 8 is an alternative embodiment of a mandrel for supporting the stent of FIG. 1 or 3.

Referring to FIG. 8, In an alternative embodiment the endcap 130 serves as a midcap 130 for supporting ends of two separate stents (an inboard and out board stent 10) supported by the mandrel during a processing step, e.g., spraying or drying. According to this embodiment, rod 14 is of sufficient length to hold two stents. For the first stent extending from the base 20 to the midcap 130 the surface 132a supports the abutting end of the stent 10. The opposing surface 132b of the midcap 130 supports an inboard end of a second stent 10 while an endcap is used to support the outboard end of the stent 10. Preferably, endcap 30 includes the pin 32 from FIG. 1 to impart the desired angular restraint of the outboard stent 10 so that the outboard stent 10 rotates with the mandrel by abutment with the pin 32.

In an alternative embodiment midcap 130 surfaces 132a, 132b may take the form of two generally cylindrical ends, each of which being similar to the end 34 described in connection with the first embodiment. Additionally, each of these end may include channels for receiving drive pins for abutting the corresponding ends of the inboard and outboard stents to cause each to rotate with the mandrel.

FIG. 9 depicts aspects of an alternative embodiment for a mandrel for supporting a stent. Illustrated is a base 120, the rod 14 and an endcap 230 having a slotted end 236 for holding the endcap 230 in a fixed position on the rod 14 as before. The endcap 230 and/or end 120 of the base 120 may serve a similar function as endcap 30 and end 20 as described earlier, except that the structure used to support the stent takes a different form. Rather than have pins 22, 32 that extend through cylindrical ends 24, 34, respectively, flanges or blades 122 and 232 are formed on planar/flat or curved surfaces at the respective ends. End 124 may form hemispherical, conical or bulbous surface having a diameter greater than the diameter of the stent 10. A raised surface, blade or flange 122 extends across the surface 124a as an integrally formed portion of the surface 124a. This blade 122 is positioned between peaks 69 of the stent 10 (FIG. 3) so as to force the stent 10 to rotate with the mandrel as the mandrel rotates. The blade 234 on the endcap 230 may also serve the purpose of causing the stent 10 to rotate. One or both blades 122, 232 may be present to strike the stent to cause it to rotate as the mandrel rotates. When there is no blade present on endcap 230, the stent may rotate relative to endcap 230 in a manner similar to the prior embodiments.

Although the above embodiments have been described in connection with a stent, it is to be understood that the present invention can be applied to devices other than stents. Medical devices to which this invention may be adapted for use includes balloon expandable stents, self-expanding stents, grafts, stent-grafts, balloons, braided or woven stents, bioabsorbable stents and catheters.

According to an alternative embodiment, the stent is mounted on a mandrel as described earlier, except that the mandrel may not have an endcap 30 when the stent is mounted thereto. The stent and mandrel are coupled to a rotary drive that is orientated to have a vertical component to its rotation axis. That is, the stent and mandrel when coupled to drive are oriented to extend upwardly so that the stent may be maintained on the mandrel by the component of gravity acting to retain the stent on the mandrel. The mandrel may then be rotated during the spraying process with the stent being retained on the mandrel. In the case of the stent and mandrel being orientated vertical, the spray nozzle may be orientated to direct coating composition slightly downward so that the stent is biased towards the base 20 by the fluidic forces acting on the stent as the stent rotates. One feature of this embodiment is the absence of the obstructing structure of an endcap, which would be disposed between the spray nozzle and stent surfaces during coating. Another feature of this embodiment would be the increased degree of relative motion between the stent and mandrel due to the absence of an endcap.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for spraying a coating composition on a stent, the stent having a first end and opposing second end and respective first and second ring structures disposed at each end, a bore, a bore diameter and a bore axis, comprising:
   mounting the stent on a mandrel support having a rotation axis including disposing a collar of the mandrel within the stent bore, the collar having a diameter that is less than the bore diameter so that the stent is free to move laterally relative to the collar, the stent resting on a surface of the collar, and the mandrel including a drive pin;
   rotating the mandrel;
   spraying the coating composition on the stent; and
   applying a force to the stent by the drive pin of the rotating mandrel striking the first end of the stent to thereby impart rotating motion to the stent about the rotation axis, whereupon after the stent has rotated through an angle the stent separates from the collar and the drive pin.

2. The method of claim 1, wherein after the stent has rotated through the angle the drive pin separates from the stent, then re-engages with the stent to rotate the stent through a second angle.

3. The method of claim 1, wherein the stent is disposed between the drive pin and an abutment of the mandrel such that the stent moves between the abutment and the drive pin, and wherein the stent displaces in a direction parallel to the rotation axis and between the abutment and drive pin when the coating composition strikes surfaces of the stent.

4. The method of claim 1, wherein the rotation axis is orientated so that gravity urges the stent towards the drive pin.

5. The method of claim 1, wherein the mandrel has the drive pin located at one end thereof and at an opposite end of the mandrel adjacent the second end of the stent the mandrel is devoid of an abutment or support for retaining the stent on the mandrel while the stent is sprayed with the coating composition so that there is no rotational restraint applied to the stent second end when the stent rotates through the angle.

6. The method of claim 1, wherein the drive pin strikes the first end of the stent when the mandrel has rotated through a distance to bring the drive pin in contact with a strut of the stent.

7. The method of claim 6, the stent mounting step including locating the drive pin within a valley of the first or second ring structure so that the drive pin strikes the stent after the drive pin has advanced a distance between at most a distance separating struts forming the valley of the first or second ring structure.

8. The method of claim 1, wherein the angle is less than 180 degrees.

9. The method of claim 8, wherein the angle is about 90 degrees.

10. The method of claim 1, wherein the drive pin is located relative to the stent so that a gap exists before the mandrel begins to rotate, the gap being such that when the coating composition is applied to the stent, fluidic forces cause the stent to move in a random pattern in response to the coating composition striking surfaces of the stent.

11. The method of claim 10, wherein the separation of the stent from the collar and drive pin includes movement about three rotational axes and in three translational directions relative to the mandrel as the mandrel rotates and fluidic forces of the coating composition strike surfaces of the stent.

12. A method for spraying a coating composition on a stent, the stent having a first ring structure at a first end and a second ring structure at a second end of the stent, the ring structures each having a repeating pattern of peaks and valleys, comprising the steps of:
   supporting the stent upon a mandrel, including the steps of
      positioning a drive pin of the mandrel between struts forming one of the valleys of the first ring structure;
      positioning an abutting end of the mandrel near the second ring structure, wherein a gap is formed between the abutment and the second ring structure or the drive pin and the struts forming the valley of the first ring structure;
   coupling the stent and mandrel to a rotary drive, the rotary drive adapted for rotating the mandrel about a rotational axis;
   rotating the mandrel about the rotational axis;
   applying the coating composition to the stent;
   wherein the stent is displaced along the rotational axis and lateral to the rotational axis relative to the mandrel as the stent rotates.

13. The method of claim 12, wherein the mandrel has a collar with an outer diameter less than a diameter of a bore of the stent so that as the mandrel rotates the stent separates from, then re-establishes contact with the collar at a new location on a surface of the collar.

14. The method of claim 12, wherein the stent is displaced along the rotational axis and lateral of the rotational axis relative to the mandrel due to the coating composition striking surfaces of the stent.

15. A stent supported on a mandrel, the stent having a ring structure at a first and second end of the stent, each ring structure having a repeating pattern of peaks and valleys, comprising:
   a first mandrel portion adapted for being coupled to a rotary drive;
   a second mandrel portion;
   a rod extending parallel to a longitudinal axis, between and connecting the first and second mandrel portions;
   a collar supported by the rod and disposed between the first and second mandrel portions for supporting the stent;
   a first drive pin extending from the first mandrel portion and in a direction approximately perpendicular to the longitudinal axis; and
   an abutment of the second mandrel portion for making abutting contact with the stent;
   wherein the drive pin and/or abutment are spaced a distance from surfaces of the stent to enable the stent to freely displace relative to the drive pin and abutment both along, and laterally of the longitudinal axis direction.

16. The stent and mandrel of claim 15, wherein the stent has a bore defining an inner diameter that is larger than a diameter of the collar so that when the stent is supported by the mandrel, the stent is free to move both parallel to, and perpendicular to the longitudinal axis.

17. The stent and mandrel of claim 15, wherein the abutment is a second drive pin angularly positioned 30 degrees from the first drive pin about the longitudinal axis so that the second drive pin is disposed at least partially within a valley of a ring structure of the stent's second end.

18. The stent and mandrel of claim 15, further including a second stent supported on the mandrel and longitudinally spaced form the first stent, wherein the first and second stents have ends supported by the second mandrel portion.

19. The stent and mandrel of claim 15, wherein the second mandrel portion has a conical, bulbous or planar surface configured to abut the stent.

20. The stent and mandrel of claim 19, wherein the second mandrel portion further includes a blade for causing the stent to rotate when the mandrel rotates.

21. The method of claim 1, wherein the stent rotates about 10 degrees about the rotational axis relative to the mandrel after the drive pin separates from the stent.

22. The stent and mandrel of claim 15, wherein the stent has a ring structure forming a valley between peaks, the valley has a first distance between struts forming the valley and a second distance between the valley low point and one of the peaks, wherein the drive pin is positioned approximately half way of the first and second distances from surfaces of the stent to form, respectively, first and second gaps.

* * * * *